US00PP29313P2

(12) United States Plant Patent
Ault

(10) Patent No.: US PP29,313 P2
(45) Date of Patent: May 22, 2018

(54) ***PANICUM* PLANT NAMED 'BAD HAIR DAY'**

(50) Latin Name: ***Panicum* hybrid**
Varietal Denomination: Bad Hair Day

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 51 days.

(21) Appl. No.: 15/330,833

(22) Filed: Nov. 7, 2016

(51) Int. Cl.
*A01H 5/12* (2018.01)

(52) U.S. Cl.
USPC ..... Plt./384
CPC ..... *A01H 5/12* (2013.01)

(58) Field of Classification Search
USPC ..... Plt./384
CPC ..... A01H 5/12
See application file for complete search history.

*Primary Examiner* — Kent L Bell
(74) *Attorney, Agent, or Firm* — Penny J. Aguirre

(57) ABSTRACT

A new cultivar of *Panicum* named 'Bad Hair Day' that is characterized by its large plant size, its upright stems that do not lodge, its dense and large inflorescences that are pendulous and arching, its foliage that is medium yellowish green in color, and its flower glumes that are yellow-green in color, and its resistance to rust.

2 Drawing Sheets

Botanical classification: *Panicum* hybrid.
Varietal denomination: 'Bad Hair Day'.

BACKGROUND OF THE INVENTION

The present invention relates to a new and distinct cultivar of *Panicum* hybrid and will be referred to hereafter by its cultivar name, 'Bad Hair Day'. 'Bad Hair Day' represents a new cultivar of switchgrass, an ornamental grass grown for landscape use.

The new cultivar of *Panicum* was derived from an ongoing controlled breeding program conducted by the Inventor in Glencoe, Ill. The objectives of the breeding program include developing new cultivars of *Panicum* with novel ornamental traits and increased drought tolerance.

'Bad Hair Day' originated as a seedling that arose from seed planted of *Panicum amarum* 'Dewey Blue' (not patented) that was pollinated with pooled pollen from numerous cultivars of *Panicum virgatum* (all unpatented) in August of 2007. The exact male parentage is therefore unknown. 'Bad Hair Day' was selected as a single unique plant in October of 2011 from amongst the resulting seedlings.

Asexual propagation of the new cultivar was first accomplished by the Inventor by rhizome division in Glencoe, Ill., in June of 2013. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bad Hair Day' as a unique cultivar of *Panicum*.

1. 'Bad Hair Day' exhibits a large plant size.
2. 'Bad Hair Day' exhibits upright stems that do not lodge.

3. 'Bad Hair Day' exhibits dense and large inflorescences that are pendulous and arching.
4. 'Bad Hair Day' exhibits foliage that is medium yellowish green in color.
5. 'Bad Hair Day' exhibits flower glumes that are yellow-green in color.
6. 'Bad Hair Day' exhibits good resistance to rust.

The female parent of 'Bad Hair Day', 'Dewey Blue' differs from 'Bad Hair Day', in having foliage that is blue-green in color, in having inflorescences that are held upright with the panicle branches mostly adpressed to the rachis, in having glumes that are blue-green fading to tan in color, and in having stems that are prone to lodging. 'Bad Hair Day' can be most closely compared to *Panicum virgatum* cultivars, 'Dallas Blues' (U.S. Plant Pat. No. 11,202), and 'Cloud Nine' (not patented). 'Cloud Nine' is similar to 'Bad Hair Day' in having large inflorescences and in being resistant to rust. 'Cloud Nine' differs from 'Bad Hair Day' in having less dense inflorescences that are held upright (not pendulous), in having glumes that are purple-pink in color, and in having foliage that is blue-green in color. 'Dallas Blues' is similar to 'Bad Hair Day' in having large inflorescences and in having a tall overall plant size. 'Dallas Blues' differs from 'Bad Hair Day' in having foliage that is blue-green in color, in having inflorescences that are held upright (not pendulous), in having glumes that are purple in color, and in being susceptible to rust.

BRIEF DESCRIPTION OF THE DRAWINGS

The accompanying colored photographs illustrate the overall appearance and distinct characteristics of the new *Panicum*. The photographs were taken of three-year-old plants of 'Bad Hair Day' as grown outdoors in a trail garden in Glencoe, Ill.

The photograph in FIG. 1 provides a side view of the overall plant habit of 'Bad Hair Day'.

Figure 1:
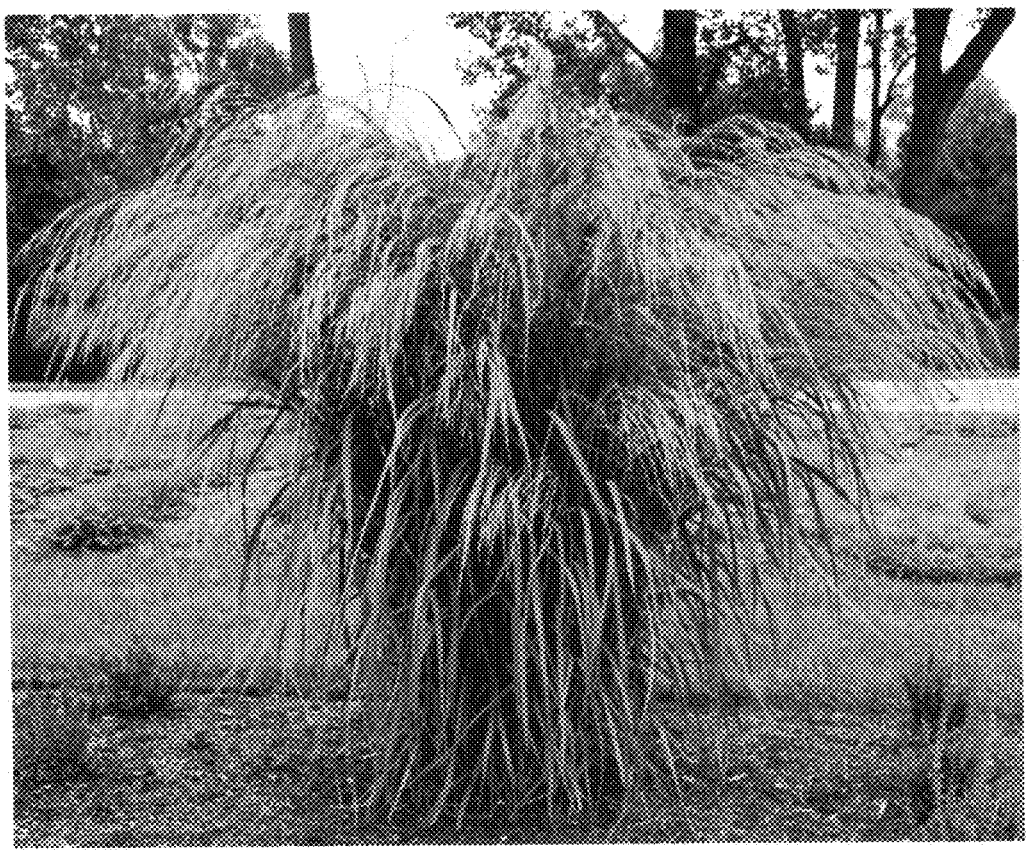
Figure 2:
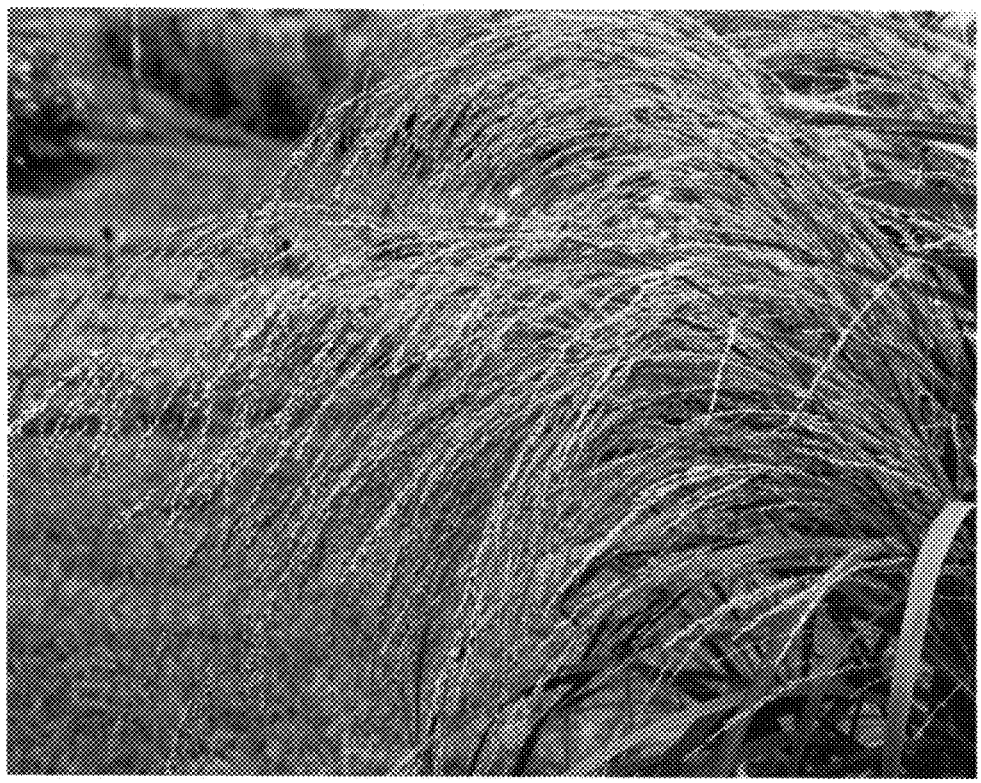

The photograph in FIG. 2 provides a close-up view of the inflorescences of 'Bad Hair Day'.

The colors in the photographs are as close as possible with the photographic and printing technology utilized and the color values cited in the Detailed Botanical Description accurately describe the colors of the new *Panicum*.

DETAILED BOTANICAL DESCRIPTION OF THE PLANT

The following is a detailed description of three-year-old plants of the new cultivar as grown outdoors in a trial garden in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From early to mid-August until mid-September with panicles persisting into the winter in northern Illinois.

*Plant type*.—Herbaceous perennial grass.

*Plant habit*.—Upright clump of foliage with flowering spikes pendulous.

*Height and width or spread*.—An average of 1.8 m in height (including inflorescences) and min spread as grown in the landscape for 3 years.

*Hardiness zone*.—At least in U.S.D.A. zones 4 to 9.

*Diseases*.—Good resistance to rust (caused by *Puccinia emaculata*) has been observed.

*Root description*.—Fibrous and fine, deeply rooted, a blend between 159B and 158C in color.

*Propagation*.—Rhizome division.

*Rhizomes*.—An average of 3 cm in length and 0.5 cm width and 155A in color.

*Growth rate*.—Vigorous for a *Panicum*.

*Time required for root development*.—From 2-inch wide divisions; up to 4 weeks for root initiation with a fully rooted plant in a 3.5-inch container produced in an average of 6 weeks.

Culm (stem) description:

*General*.—Cylindrical, hollow pith, thin but strong, held erect.

*Culm number*.—An average of 8 in an 8-cm container, forming a tight clump.

*Culm color*.—A blend between 138A to 138B and 144C in summer, 162A with base 161B to 161C in winter, ranges from 13 cm to 20 cm of exposed area between leaf nodes.

*Culm size*.—An average of 6.5 mm in diameter and 150 cm in height from the base to the base of the peduncle.

*Culm surface*.—Glabrous, smooth, and slightly striate.

*Internode length*.—An average of 22 cm.

Foliage description:

*Leaf shape*.—Narrowly lanceolate.

*Leaf division*.—Simple.

*Leaf margin*.—Entire, scaberulose.

*Leaf base*.—Sheathed to base of the node.

*Leaf venation*.—Parallel, not distinguishable in color from leaf coloration.

*Leaf width*.—An average of 1.5 cm at widest section.

*Leaf length*.—Blade; an average of 60 cm, sheathed portion; an average of 21 cm.

*Leaves per culm*.—An average of 5 on flowering culms.

*Leaf color*.—Upper and lower surfaces a color between 138A and 139B.

*Leaf surface*.—Glabrous, dull, and slightly striate on both surfaces.

*Ligule*.—An average of 1.5 mm in height and 5 mm in width, color on both surfaces; 163D with 165A to 165B at the top, covered in fine hairs on the inner surface that protrude from the top, NN155C in color.

Flower description:

*Inflorescence type*.—Dense, spreading panicle at terminus of stem, symmetrical, typically 2-flowered spikelet with lower spikelet male and upper spikelet hermaphroditic.

*Inflorescence color*.—Overall color of the raceme is 138B in early summer, maturing to a blend of 145A and 145B, turns to 161A in the late fall.

*Inflorescence size*.—An average of 65 cm in length and 25 cm in width.

*Inflorescence arrangement*.—Pendulous, widely arching outwards.

*Spikelet description*.—An average of 200 per panicle, oval to elliptic in shape, an average of 5 mm in length and 1.5 mm in width, awn present; an average of 0.5 mm in length and 61A in color, lower glume; an average of 4 mm in length and 1 mm in width, upper glume and lower lemma; an average of 4.5 cm in length and 1 mm width, color; glumes and lemma upper and lower surface a blend between 144D and 157B suffused with 165B near the base, palea; an average of 1.5 mm in length and 0.5 mm in width, translucent and glossy, color a blend between 155C and 157D, glumes, lemma, and palea are oval to elliptic in shape and convex with all surfaces glabrous and smooth.

*Rachis*.—An average of 45 cm in length from last leaf, raceme portion; an average of 27 cm in length and 1 mm in width, glabrous and smooth surface, a blend between 138B and 143B in color, lateral branches (peduncle-like); an average of 7, about 0.2 mm in width and an average of 18 cm in length (shortest at terminus), 138B in color, glabrous surface, pedicel; an average of 5 mm in length and 0.2 mm in width, very fine and wiry, 138B in color, glabrous surface.

Reproductive organs:

*Androecium*.—Anthers; 3, an average of 2 mm in length and 0.5 mm in width, 172A in color, basifixed on very fine, translucent filament, pollen; moderate in quantity and 162C in color.

*Gynoecium*.—Pistil; 1, 2 plumose stigmas on short, fine styles adnate to ovary, stigma N79B to N79C in color, an average of 1 mm in length and 0.5 mm in width, ovary; 1-locular, superior, an average of 2.5 mm in length and 1 mm in with, 149D in color.

It is claimed:

1. A new and distinct cultivar of *Panicum* plant named 'Bad Hair Day' as herein illustrated and described.

* * * * *